United States Patent
Gefter et al.

(10) Patent No.: US 6,759,234 B1
(45) Date of Patent: Jul. 6, 2004

(54) COMPOSITIONS AND METHODS FOR ADMINISTERING TO HUMANS, PEPTIDES CAPABLE OF DOWN REGULATING AN ANTIGEN SPECIFIC IMMUNE RESPONSE

(75) Inventors: Malcolm L. Gefter, Lincoln, MA (US); Ze'ev Shaked, Berkeley, CA (US); Malcolm Morville, Shrewsbury, MA (US)

(73) Assignee: Immulogic Pharmaceutical Corporation, Waltham, MA (US)

( * ) Notice: Subject to any disclaimer, the term of this patent is extended or adjusted under 35 U.S.C. 154(b) by 0 days.

(21) Appl. No.: 08/300,510

(22) Filed: Sep. 2, 1994

(51) Int. Cl.[7] .......................... A61K 38/16; A61K 39/35
(52) U.S. Cl. ................................ 435/275.1; 424/185.1; 514/12; 514/13; 514/14
(58) Field of Search .......................... 424/184.1, 185.1, 424/275.1, 276.1; 530/300, 350, 395, 868; 514/12, 13, 14

(56) References Cited

U.S. PATENT DOCUMENTS

| | | | |
|---|---|---|---|
| 4,338,297 A | | 7/1982 | Michael |
| 5,328,991 A | * | 7/1994 | Kuo et al. .................. 530/403 |
| 5,547,669 A | * | 8/1996 | Rogers et al. ........... 424/185.1 |
| 5,710,126 A | * | 1/1998 | Griffith et al. ................. 514/12 |

FOREIGN PATENT DOCUMENTS

| | | | |
|---|---|---|---|
| WO | 9308280 | * | 4/1993 |
| WO | 9319178 | * | 9/1993 |
| WO | WO A 9321321 | | 10/1993 |
| WO | WO A 9411512 | | 5/1994 |
| WO | WO A 9421675 | | 9/1994 |
| WO | WO A 9427634 | | 12/1994 |
| WO | WO A 9506728 | | 3/1995 |

OTHER PUBLICATIONS

Briner et al, Proc. Natl. Acad. Sci. USA, 90, 7608–7612, 1993.*
Janeway et al, Immunobiology: The Immune System in Health and Disease, 4th Ed., 1999, pp. 121–123.*
Berzofsky, Jay A., et al., *Letters to Nature*, vol. 334, Aug. 25, 1988, pp. 706–708.
Berzofsky, Jay A., *The Journal of Clinical Investigation, Inc.*, vol. 82, Dec., 1988, pp. 1811–1817.
Clark, et al., *Nature*, vol. 367, Feb. 3, 1994, pp. 425–428.
Ferguson, T. A., et al., *Cellular Immunology*, vol. 78, 1983, pp. 1–3.
Hedlin, Gunilla, et al., *J. Allergy Clin. Immunol.*, vol. 84, No. 3, Sep. 1989, pp. 390–399.
Higgins, Julia A., et al., *J. Allergy Clin. Immunol.*, vol. 93, No. 5, May 1994, pp. 891–899.
Ishizaka, Kimishige, et al., *The Journal of Immunology*, vol. 113, No. 1, Jul. 1974, pp. 70–77.
Ishizaka, Kimishige, et al., *The Journal of Immunology*, vol. 114, part 1, Jan. 1975, pp. 110–115.
Jenkins, Marc K., et al., *Current Opinion in Immunology*, vol. 5, 1993, pp. 361–367.
Katz, D. H., *Immunology*, vol. 41, pp. 1–24.
Lew, Andrew M. et al., *The Journal of Immunology*, vol. 142, No. 11, Jun. 1, 1989, pp. 4012–4016.
Litwin, Allen, et al., *Int. Arch. Allergy Appl. Immunol.*, 1988, vol. 87, pp. 361–366.
Litwin, A., et al., *Clinical and Experimental Allergy*, vol. 21, 1991, pp. 457–465.
Margalit, Hanah, et al., *The Journal of Immunology*, vol. 138, No. 7, Apr. 1, 1987, pp. 2213–2229.
Marsh, D. G., et al., *Immunology*, vol. 18, 1970, pp. 705–722.
Metzger, W. James, et al., *The New England Journal of Medicine*, Nov. 18, 1976, pp. 1160–1164.
Michael, J. G., et al., *Clinical and Experimental Allergy*, 1990, vol. 20, pp. 669–674.
Norman, Philip S., et al., *J. Allergy Clin. Immunol.*, Oct., 1982, vol. 9, No. 4, pp. 248–260.
Ota, Kohei, et al., *Letters to Nature*, 1990.
Rothbard, Jonathan B., et al., *The EMBO Journal*, vol. 7, No. 1, 1988, pp.93–100.
Sehon, A. H., et al., Postgraduate course presentation, *J. Allergy Clin. Immunol.*, Oct. 1979, vol. 64, No. 4, pp. 242–250.
Standring, R. et al., *Int. Arch. Allergy Appl. Immunol.*, 1988, vol. 87, pp. 337–341.
Takatsu, Kiyoshi, et al., The Journal of Immunology, 1975, vol. 115, No. 6, pp. 1469–1476.

* cited by examiner

*Primary Examiner*—David Saunders
(74) *Attorney, Agent, or Firm*—Lahive & Cockfield, LLP; Amy E. Mandragouras, Esq.; Jane E. Remillard, Esq.

(57) ABSTRACT

The present invention provides therapeutic compositions and methods for treating disease conditions in humans associated with an antigen specific immune response by the human to an antigen such as a protein antigen (i.e. allergy and autoimmune diseases). Therapeutic compositions of the invention are reproducible preparations which are suitable for human therapy. Compositions of the invention comprise at least one isolated peptide having a defined sequence of amino acid residues and the composition is capable of down regulating an antigen specific immune response to an offending antigen in a population of humans subject to the antigen specific immune response. Compositions and methods of the invention may be used to treat sensitivity to protein allergens in humans and may also be used to treat autoimmune disease such as rheumatoid arthritis, diabetes, myasthenia gravis, Grave's disease, Good Pasture's syndrome, thyroiditis and multiple sclerosis.

20 Claims, 1 Drawing Sheet

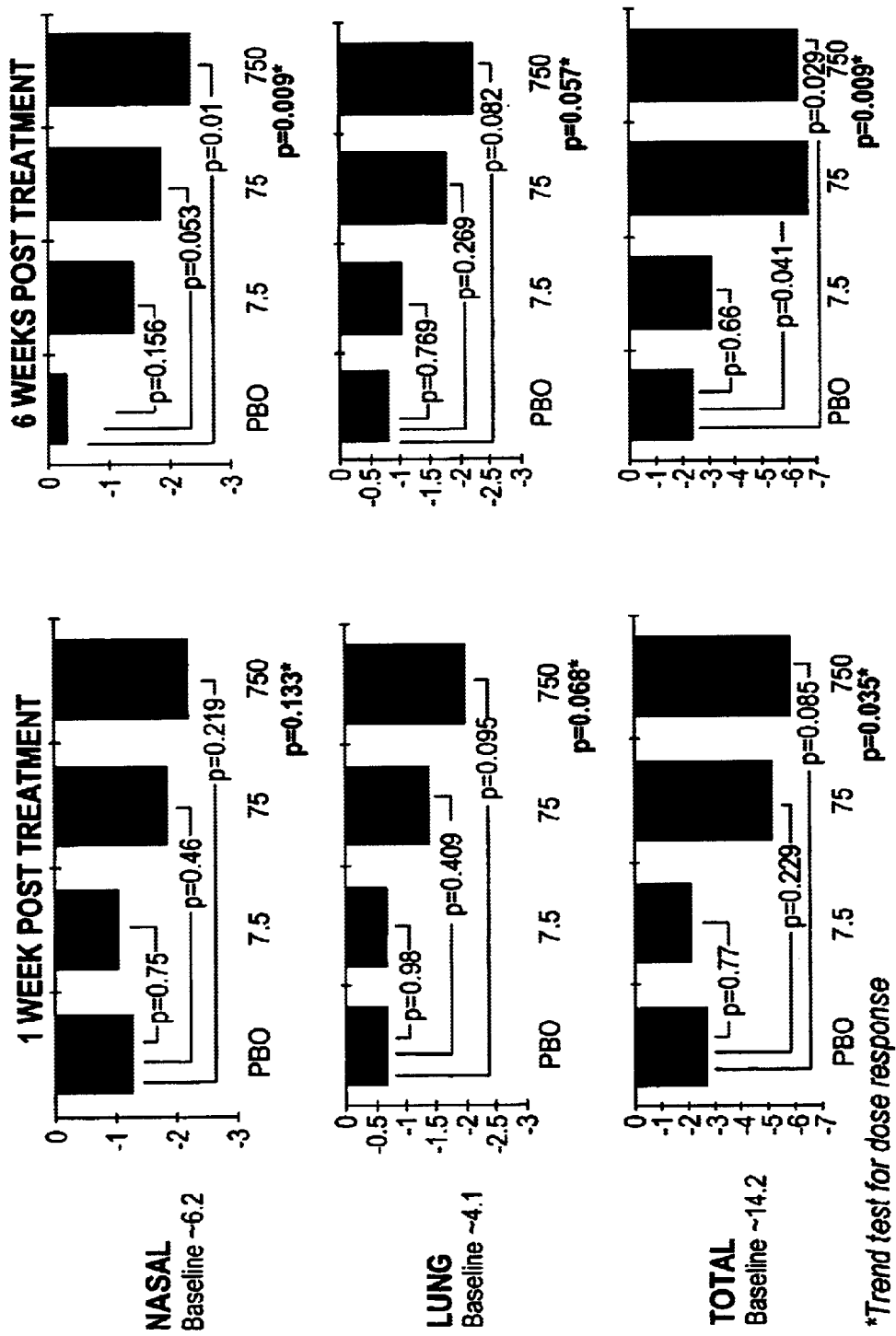

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 27 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:1:

```
Lys Arg Asp Val Asp Leu Phe Leu Thr Gly Thr Pro Asp Glu Tyr Val
1               5                   10                  15

Glu Gln Val Ala Gln Tyr Lys Ala Leu Pro Val
            20                  25
```

(2) INFORMATION FOR SEQ ID NO:2:

(i) SEQUENCE CHARACTERISTICS:
      (A) LENGTH: 27 amino acids
      (B) TYPE: amino acid
      (D) TOPOLOGY: linear (ii) MOLECULE TYPE: peptide (v) FRAGMENT TYPE: internal (xi) SEQUENCE DESCRIPTION: SEQ ID NO:2:

```
Lys Ala Leu Pro Val Val Leu Glu Asn Ala Arg Ile Leu Lys Asn Cys
1               5                   10                  15

Val Asp Ala Lys Met Thr Glu Glu Asp Lys Glu
            20                  25
```

COMPOSITIONS AND METHODS FOR ADMINISTERING TO HUMANS, PEPTIDES CAPABLE OF DOWN REGULATING AN ANTIGEN SPECIFIC IMMUNE RESPONSE

BACKGROUND OF THE INVENTION

Allergies have been the bane of human existence since the beginning of human history. Those individuals afflicted with allergies suffer with continual or repeated bouts of sinusitis, rhinitis, itchy watery eyes, nose and mouth, and allergic asthma which may be so severe as to cause hospitalization. The most dangerous human allergic response is anaphylaxis, which will cause death without medical intervention.

Pharmaceuticals to alleviate many of the less severe symptoms have been developed such as oral administration of antihistamines, inhalers for asthma, and portable injection kits containing adrenaline to suppress anaphylactic shock until medical help can be reached. However, these pharmaceuticals do nothing more than mask the symptoms caused by histamine release, the end result of the human immune response which begins when the offending allergen enters the body. Furthermore, many of the more powerful antihistamine drugs have undesirable side effects such as excessive dryness of the mucosa or drowsiness.

Over the past several decades a therapy involving desensitization of humans has been developed. Desensitation therapy involves repeated injections with increasing dosages of a crude allergen extract of the offending allergen. Although treatment with allergen extracts has been proven somewhat effective in the clinic for alleviating allergen-related symptoms, and is a common therapy used most widely in allergy clinics today, the mechanism of desensitization remains unclear. Furthermore, desensitization therapy must be undertaken with extreme caution as the side effects may be significant or even fatal (i.e. anaphylaxis). Thus, it is necessary for the patient to undergo multiple injections of incrementally larger dosages of the crude extract, and remain under medical observation for one or more hours every time an injection is given. In addition, it is often necessary for an allergic patient to receive treatment until maintenance dose is reached which usually requires treatment injection once a week for six to twelve months and at intervals of four to six weeks thereafter. Thus, this treatment is very time intensive, inconvenient and not without side effects or danger for the patient.

In an attempt to make desensitization immunotherapy more effective and safer, several investigators have attempted to develop modified allergens with the intention of effecting the immunological events which occur during immunotherapy (i.e. to increase blocking IgG antibodies or decrease the number of allergen specific IgE antibodies). Such modifications include preparing and testing: urea-denatured allergens, Ishizaka et al, *E. J. Immunol.* 114:100–115 (1975); allergoids created by formalin treatment of allergens; Norman et al., *J Allergy Clin Immunol*, 70:248–260 (1982); allergens bound to tolerogens such as D-glutamic acid-D-lysine, Katz D., *Immunology*, 41:1–24 (1980);or polyethyleneglycol, Sehon et al, *J Allergy Clin Immunol* 64:242–250 (1979); and glutaraldehyde-polymerized allergens, Metzger et al. *N Engl J Med* 295:1160–1164 (1976).

Michael et al., U.S. Pat. No. 4,338,297, disclose a polypeptide active pollen immunosuppressant prepared by proteolytic enzyme digestion of pollen antigen and purified by reaction with antipollen antibody potentially for use as a therapeutic in desensitization. Later, the same group published experiments indicating that it was possible to suppress the immune response in mice to protein antigens such as bovine serum and honey bee venom phospholipase A2 by treatment with fragments derived by enzymatic digestion (Michael et al., *J Clin Immunol*, 75:200(abstr) (1985), and Ferguson et al., *Cell Immunol*, 78:1–12 (1983)), and in addition found that fragmenting allergenic proteins of short ragweed pollen by peptic digestion and administering digestion products in the molecular weight range of 5–15 kD either prior to, or after intraperitoneal immunization with a ragweed preparation resulted in suppression of the immune response (Michael et al., *Clin Exp Allergy*, 20:669–674 (1990)). According to Michael et al., it was believed that the suppression of the immune response to the ragweed preparation involved T cells, and that the fragments of the peptic digest were capable of stimulating T cells that regulate immunosuppression.

In addition, the same group of investigators tested a composition comprising peptic fragments of short ragweed for clinical effectiveness in humans, (Litwin et al. *Clin Exp Allergy* 21:457–465 (1991)). In this study, three groups of ragweed hay fever patients were placed on pre-seasonal immunotherapy. One group received a conventional ragweed preparation that had been enriched for ragweed antigen (Amb a I) designated Pool 2. The proteins in Pool 2 contained about 26% Amb a I. Pool 2 was enzymatically digested and a fraction containing proteins in the 10kD range or less was used as the peptic fragment composition and designated fSRW. The third group was given a placebo. Although the results indicated that the groups given either Pool 2 or fSRW had significantly reduced symptom-medication scores compared with the placebo-treatment group, the differences between the fSRW treatment and the Pool 2 treatment were not significant. Thus, the fSRW peptic digest composition did not totally achieve its goal of providing significant efficacy or convenience over a conventional immunotherapy composition comprising a crude extract of the allergen to which the individual is sensitive, and has not been thus far approved for use in the United States or is such a peptic composition presently the subject of a clinical study in the United States.

Furthermore, the use of a composition comprising peptic fragments of a protein allergen such as that described by Litwin et al. has serious drawbacks. For example the protein extract (Pool 2) which was digested to produce the fSRW peptide composition was enriched for the desired Amb a I protein to only 26% and any number of other proteins and contaminants were likely present in the Pool 2 composition and were carried over to the fSRW digest. According to Litwin et al., the precise Amb a I content in fSRW could not be determined because components of the fSRW did not remain in solution. Thus the fSRW may have contained undesirable proteins which may have adverse effects on the patients being treated, and therefore, provides no advantage over the use of a conventional crude extract, and moreover, may have many of the same disadvantages associated with classic immunotherapy. In addition, the enzymatic digest of a crude protein does not consistently produce the same composition of peptides every time. Therefore, it would be almost impossible to produce consistent, precisely-defined, highly purified compositions of peptides for use as a pharmaceutical for human treatment as is required by most regulatory agencies throughout the world using a composition of enzymatically digested proteins, similar to that of fSRW described by Litwin et al.

In addition, similar to allergy, autoimmnune diseases such as Type I diabetes, multiple sclerosis, and rheumatoid artritis are generally accepted as being the result of an antigen specific T cell mediated response against an antigen which in the case of autoimmune disease, is the body's own tissue. Therefore, it is believed an approach to treating autoimmune disease which is conceptually similar to that for treating allergies would be appropriate. For example, WO 88/10120, WO 91/08760, WO 92/06704, WO 93/21222, and WO 94/07520, describe oral or enteral administration of whole autoantigens, or fragments thereof such as mylein basic protein, (MBP a presumed autoantigen in multiple sclerosis), insulin for the treatment of diabetes, or collagen for the treatment of rheumatoid arthritis. For many of the reasons described above, there are limits to the clinical applicability of oral, enteral or aerosol administration of autoantigens such as an inability to characterize the active component of a thereapeutic composition once introduced in the stomach due to subsequent enzymatic degradation in the stomach. Thus, predictable and reproducible therapeutic effects may be difficult to achieve using these methods, not to mention the potential for adverse side effects as a result of the body's further processing of the therapeutic which may not be predictable.

The present invention overcomes the drawbacks described above and provides methods for treating allergies and other diseases associated with an immune response by the human to a protein antigen (i.e. autoimmune diseases), using precisely-defined, highly purified, preparations comprising at least one peptide having a defined sequence of amino acid residues which comprises at least one T cell epitope of the protein antigen, administered in non-immunogenic form. Preferred, compositions and methods of treating humans in accordance with the present invention have been tested in the clinic and have been shown to be successful. The ramifications of these successful clinical trials are expected to change the face of allergy immunotherapy forever, as well as change the course of treatment of autoimmune diseases and other areas relating to human disease conditions associated with the immune response.

SUMMARY OF THE INVENTION

The present invention provides therapeutic compositions and methods for treating disease conditions in humans associated with an antigen specific immune response by the human to an antigen such as a protein antigen (i.e. allergy and autoimmune diseases). Therapeutic compositions of the invention are precisely-defined, highly purified reproducible preparations which are suitable for human therapy. Preferred compositions of the invention comprise at least one isolated, purified peptide, free from all other polypeptides or contaminants, the peptide having a defined sequence of amino acid residues which comprise at least one T cell epitope of an antigen of interest. A therapeutic composition of the invention is capable of down regulating an antigen specific immune response to an antigen of interest in a population of humans subject to the antigen specific immune response such that disease symptoms are reduced or eliminated, and/or the onset or progression of disease symptoms is prevented or slowed.

Compositions and methods of the invention may be used to treat sensitivity to protein allergens in humans such as allergies to ragweed, grasses, trees, house dust mite (dust), cats, dogs and other animals, and any other airborne or contact allergens. Compositions and methods of the invention may also be used to treat autoimmune disease such as rheumatoid arthritis, diabetes, myasthenia gravis, Grave's disease, Good Pasture's syndrome, thyroiditis and multiple sclerosis.

BRIEF DESCRIPTION OF THE DRAWINGS

FIG. 1 is a graphic representation of catroom symptom aggravation (nasal, lung, and total allergy) at one and six weeks post treatment with pairwise comparisons versus placebo (PBO) for total allergy symptoms at 75 $\mu$g and 750 $\mu$g at six weeks, trend tests for dose response at one and six weeks for total allergy symptoms are indicated (see starred data).

DETAILED DESCRIPTION OF THE INVENTION

The patent and scientific literature referred to herein establishes the knowledge that is available to those with skill in the art. The issued U.S. patents, PCT publications, and other publications cited herein are hereby incorporated by reference.

The present invention provides therapeutic compositions and methods for treating disease conditions in humans associated with an immune response by the human to an antigen. Therapeutic compositions of the invention comprise at least one isolated, purified peptide, free from all other proteins or contaminants, and having a defined sequence of amino acid residues which comprise at least one T cell epitope of the antigen. As used herein, the term "isolated" refers to a peptide which is free of all other polypeptides, contaminants, starting reagents or other materials, and which is unconjugated to any other molecule. The composition or compositions of the invention when administered to a patient in a therapeutic regimen in non-immunogenic form, are capable of down regulating an antigen specific immune response in a population of humans subject to the antigen specific immune response.

Compositions and methods of the invention may be used to treat disease conditions relating to antigens, such as protein allergens, in humans i.e. allergies to ragweed, grasses, trees, house dust mite (dust), cats, dogs and other animals, and any other airborne or contact allergens. Human clinical trials described in the Examples discuss the successful use of compositions and methods of the invention in the treatment of humans allergic to cats. This invention may also be used to treat autoimmune disease such as rheumatoid arthritis, diabetes, myasthenia gravis, Grave's disease, Good Pasture's syndrome, psoriasis, thyroiditis and multiple sclerosis wherein the antigen responsible for the disease is a protein autoantigen.

In accordance with this invention, a "peptide" refers to a defined sequence of amino acid residues preferably comprising no more than about 50 amino acid residues and comprising at least approximately seven amino acid residues in length, and preferably at least about 12–40 amino acid residues in length, and more preferably at least 13–30 amino acid residues in length and which, when derived from a protein antigen, contains less than the amino acids of the entire protein antigen and preferably no more than about 75% of the amino acid residues of the entire protein antigen. Peptides used in accordance with the invention comprise at least one T cell epitope of an antigen. A T cell epitope is the basic element or smallest unit of recognition by a T cell receptor, where the epitope comprises amino acids essential to receptor recognition. T cell epitopes arc believed to be involved in the initiation and perpetuation of the immune response to an antigen such as a protein allergen which is responsible for the clinical symptoms of allergy. These T cell epitopes are thought to trigger early immune response events at the level of the T helper cell by binding to an appropriate HLA molecule on the surface of an antigen presenting cell and stimulating the relevant T cell subpopulation. These events lead to T cell proliferation, lymphokine secretion, local inflammatory reactions, recruitment of additional immune cells to the site, and activation of the B cell cascade leading to production of antibodies. One isotype of these antibodies, IgE is fundamentally important to the development of allergic symptoms and its production is influenced early in the cascade of events, at the level of the T helper cell by the nature of the lymphokines secreted. In the case of an autoimmune disease, the antibodies produced are autoantibodies against an autoantigen resulting in the clinical symptoms of an autoimmune disease i.e. autoantibodies directed against myelin basic protein, a presumed autoantigen in multiple sclerosis.

A therapeutic/prophylactic treatment regimen in accordance with the invention (which results in prevention of, or delay in, the onset of disease symptoms caused by an offending antigen or results in reduction, progression, or alleviation of symptoms caused by an offending antigen i.e. down regulation of an antigen specific immune response) comprises administration, in non-immunogenic form (e.g. without adjuvant) of a therapeutic composition of the invention comprising at least one isolated peptide which may be derived from a protein antigen responsible for the disease condition being treated (or a peptide derived from an immunologically cross-reactive protein antigen). While not intending to be limited to any theory, it is believed that administration of a therapeutic composition of the invention may: a) cause T cell non responsiveness of appropriate T cell subpopulations such that they become unresponsive to the offending antigen and do not participate in stimulating an immune response upon exposure to the offending protein antigen (i.e. via anergy or apoptosis); b) modify the lymphokine secretion profile as compared with exposure to the naturally occurring offending antigen (e.g. result in a decrease of IL-4 and/or an increase in IL-2); c) cause T cell subpopulations which normally participate in the response to the offending antigen to be drawn away from the sites of normal exposure (e.g. nasal mucosa, skin and lung for allergy) towards the sites of administration of the composition (this redistribution of T cell subpopulations may ameliorate or reduce the ability of an individual's immune system to stimulate the usual immune response at the site of normal exposure to the offending antigen, resulting in diminution in allergic symptoms); or d) cause induction of T suppressor cells.

While not intending to be limited to any theory, it is believed that down regulation of an antigen specific immune response is induced as a result of not providing an appropriate costimulatory signal sometimes referred to as a "second signal". Briefly, it is believed that stimulation of T cells requires two types of signals, the first is the recognition by the T cell via the T cell receptor of appropriate MHC-associated processed antigens on antigen presenting cells (APCs) and the second type of signal is referred to as a costimulatory signal(s) or "second signal" which may be provided by certain competent APCs. When a composition of the invention is administered without in non-immunogenic form (e.g. without adjuvant), it is believed that competent APCs which are capable of producing the second signal or costimulatory signal are not engaged in the stimulation of appropriate T cells therefore resulting in T cell non responsiveness or reduced T cell responsiveness. In addition, there are a number of antibodies or other reagents capable of blocking the delivery of costimulatory signals such as the "second signal" which include, but are not limited to B7 (including B7-1, B7-2, and BB-1), CD28, CTLA4, CD40 CD40L CD54 and CD11a/18 (Jenkins and Johnson, *Current Opinion in Immunology*, 5:361–367 (1993), and Clark and Ledbetter, *Nature*, 367:425–428 (1994)) Thus, in accordance with the invention a composition may be administered in nonimmunogenic form as discussed above, in conjunction with a reagent capable of blocking costimulatory signals such that the level of T cell non responsiveness is enhanced.

Compositions and methods of the invention are useful for treating humans for allergies to any number of protein allergens such as: a protein allergen of the genus Dermatophagoides; a protein allergen of the genus Felis; a protein allergen of the genus Ambrosia; a protein allergen of the genus Lolium; a protein allergen of the genus Cryptomeria; a protein allergen of the genus Alternaria; a protein allergen of the genus Alder; a protein allergen of the genus Betula; a protein allergen of the genus Quercus; a protein allergen of the genus Olea; a protein allergen of the genus Artemisia; a protein allergen of the genus Plantago; a protein allergen of the genus Parietaria; a protein allergen of the genus Canine; a protein allergen of the genus Blattella; a protein allergen of the genus Apis; a protein allergen of the genus Cupressus; a protein allergen of the genus Juniperus; a protein allergen of the genus Thuya; a protein allergen of the genus Chamaecyparis; a protein allergen of the genus Periplaneta; a protein allergen of the genus Agropyron; a protein allergen of the genus Secale; a protein allergen of the genus Triticum; a protein allergen of the genus Dactylis; a protein allergen of the genus Festuca; a protein allergen of the genus Poa; a protein allergen of the genus Avena; a protein allergen of the genus Holcus; a protein allergen of the genus Anthoxanthum; a protein allergen of the genus Arrhenatherum; a protein allergen of the genus Agrostis; a protein allergen of the genus Phleum; a protein allergen of the genus Phalaris; a protein allergen of the genus Paspalum; and a protein allergen of the genus Sorghum.

Examples of various known protein allergens derived from some of the above-identified genus include: Dermatophagoides (pteronyssinus or farinae) Der p I; Der p II; Der p III; Der p VII; Der f I; Der f II; Der f III; Der f VII; Felis (domesticus) Fel d I; Ambrosia (artemiisfolia) Amb a I.1; Amb a I.2; Amb a I.3; Amb a I.4; Amb a II; Lollium (perenne) Lol p I; Lot p II; Lol p III; Lot p IV; Lol p IX (Lol p V or Lol p Ib); Cryptomeria (japonica) Cry j I; Cry j II; Can f I; Can f II; Juniperus (sabinoides or virginiana) Jun s I; Jun v I; Dactylis (glomerata) Dac g I; Poa (pretensis) Poa p I; Phl p I; and Sorghum (halepensis) Sor h I.

Peptides having a defined sequence of amino acid residues comprising at least one T cell epitope and which induce T cell non responsiveness or reduced T cell responsiveness, have been identified and isolated for many of the above named protein allergens and are useful in compositions and methods of the present invention. For example, peptides comprising T cell epitopes derived from Der p I; Der p II, Der f I; and Der f II are disclosed in U.S. Ser. No. 08/227,772 (abandoned) and U.S. Ser. No. 07/963,381 (abandoned) incorporated herein by reference, and published in WO93/08279. Peptides comprising T cell epitopes derived from Fel d I are disclosed in U.S. Ser. No. 07/662,276 (abandoned), 07/884,718 (abandoned), and 08/006,116 (abandoned) all incorporated herein by reference. Peptides comprising T cell epitopes derived from Amb a I.1; Amb a I.2; Amb a I.3; Amb a I.4; and Amb a II are disclosed in U.S. Ser. No. 07/866,679 (abandoned) and WO93/21321 incorporated herein by reference. Peptides comprising T cell epitopes derived from Lol p I, Dac g I, Poa p I, and Phl p I are disclosed in U.S. Ser. No. 08/031,001 (abandoned) and peptides comprising T cell epitopes derived from Lol p IX (Lol p V or Lol p Ib) are disclosed in WO94/04564, and 08/106,016 abandoned incorporated herein by reference. Peptides comprising T cell epitopes derived from Cry f I and Cry j II, and Jun s I and Jun v I are disclosed in U.S. Ser. No. 08/226,248 abandoned incorporated herein by reference. Peptides comprising T cell epitopes derived from Can f I and Can f II are disclosed in U.S. Ser. No. 08/156,549 (abandoned) incorporated herein by reference. Peptides comprising T cell epitopes derived from Sor h I are disclosed in AU93/00559.

A number of antigens (i.e. autoantigens) have been found to cause disease symptoms in autoimmune diseases (i.e. autoantigens such as insulin; myelin basic protein; rh factor; acetylcholine receptors; thyroid cell receptors; basement membrane proteins; thyroid proteins; ICA-69 (PM-1); glutamic acid decarboxylase (64K or 65 K); proteolipid protein (PLP), myelin associated glycoprotein (MAG), Collagen (Type II), Heat Shock Protein and carboxypeptidase H) in autoimmune diseases such as diabetes, rheumatoid arthritis, and multiple sclerosis. For example, peptides which may comprise T cell epitopes derived from myelin oligodendrocyte protein MOG, a protein which is believed to be one of the autoantigens involved in multiple sclerosis are disclosed in U.S. Ser. No. 08/116,824 incorporated herein by reference. Peptides which are believed to be able to down regulate the antigen specific response to MBP (myelin basic protein), a protein believed to be an autoantigen in multiple sclerosis have been identified in WO 93/21222, EP 0 304 279, WO 91/15225, Ota et al, Letters to Nature, 346:183–187 (1990), Wucherpfennig et al., J. Exp. Med., 170:279–290 (1994). Peptides which are believed to be able to down regulate the antigen specific response to soluble Type II collagen, a protein antigen believed to be an autoantigen in rheumatoid arthritis, have been identified in WO 94/07520. WO 92/06704 describes methods for identifying peptides of insulin, which are believed to be effective and the treatment and prevention of Type I diabetes.

In addition, peptides having defined amino acid compositions and which comprise T cell epitopes, may be identified for any protein antigen or autoantigen. One method includes dividing the protein antigen into non-overlapping, or overlapping peptides of desired lengths and synthesizing, purifying and testing those peptides to determine whether the peptides comprise at least one T cell epitope using any number of assays (i.e. T cell proliferation assays, lymphokine secretion assays, and T cell non-responsiveness studies). In another method an algorithm is used for predicting those peptides which are likely to comprise T cell epitopes and then synthesizing, purifying and testing the peptides predicted by the algorithm in T cell assays to determine if such predicted peptides cause T cell proliferation or lymphokine secretion, or T cell non-responsiveness and are therefore likely to contain T cell epitopes. As discussed in many of the documents cited above, human T cell stimulating activity can be tested by culturing T cells obtained from an individual sensitive to a predetermined protein antigen (i.e. an allergen or an autoantigen) with a peptide derived from the antigen and determining whether proliferation of T cells occurs in response to the peptide as measured, e.g., by cellular uptake of tritiated thymidine. Stimulation indices for responses by T cells to peptides can be calculated as the maximum counts per minute (CPM) in response to a peptide divided by the control CPM. A T cell stimulation index (S.I.) equal to or greater than two times the background level is considered "positive". Positive results are used to calculate the mean stimulation index for each peptide for the group of peptides tested. Preferred peptides useful in accordance with this invention comprise at least one T cell epitope and preferably at least two or more T cell epitopes and have a mean T cell stimulation index of greater than or equal to 2.0. A peptide having a T cell stimulation index of greater than or equal to 2.0 is considered useful as a therapeutic agent. Preferred peptides have a mean T cell stimulation index of at least 2.5, more preferably at least 3.5, even more preferably at least 4.0, and most preferably at least 5.0.

In addition, preferred peptides have a positivity index (P.I.) of at least about 100, more preferably at least 150, even more preferably at least about 200 and most preferably at least about 250. The positivity index for a peptide is determined by multiplying the mean T cell stimulation index by the percent of individuals, in a population of individuals tested sensitive to the antigen being tested (e.g., preferably at least 9 individuals, more preferably at least 16 individuals or more, more preferably at least 20 individuals or more, or even more preferably at least 30 individuals or more), who have T cells that respond to the peptide. Thus, the positivity index represents both the strength of a T cell response to a peptide (S.I.) and the frequency of a T cell response to a peptide in a population of individuals sensitive to the antigen being tested.

One algorithm for predicting peptides having T cell stimulating activity which has been used with success is reported in Rothbard, 1st Forum in Virology, Annals of the Pasteur Institute, pp 518–526 (December, 1986), Rothbard and Taylor, Embo, 7:93–100 (1988), and EP 0 304 279. These documents report defining a general T cell pattern (algorithm), its statistical significance and its correlation with known epitopes as well as its successful use in predicting previously unidentified T cell epitopes of various protein antigens and autoantigens. The general pattern for a peptide known to bind Class II MHC well as reported in the above-mentioned documents appears to contain a linear pattern composed of a charged amino acid residue or glycine followed by two hydrophobic residues. After determining if a peptide conforms to the general pattern, the peptide can then be tested for T cell reactivity. Other algorithms that have been used to predict T cell epitopes of previously undefined proteins include an algorithm reported by Margalit et al., J. Immunol., 138:2213–2229 (1987), which is based on an amphipathic helix model.

Additionally, peptides comprising "cryptic epitopes" may be determined and are also useful in accordance with the methods of this invention. Cryptic epitopes are those determinants in a protein antigen or protein autoantigen which, due to processing and presentation of the native protein antigen to the appropriate MHC molecule, are not normally revealed to the immune system. However, a peptide comprising a cryptic epitope is capable of causing T cells to become non-responsive, and when a subject is primed with the peptide, T cells obtained from the subject will proliferate in vitro in response to the peptide or the protein antigen from which the peptide is derived. Peptides which comprise at least one cryptic epitope derived from a protein antigen or autoantigen are referred to herein as "cryptic peptides". To confirm the presence of cryptic epitopes a T cell proliferation assay may be used as is known in the art and is described above. In this assay, antigen-primed T cells are cultured in vitro in the presence of each peptide separately to establish peptide-reactive T cell lines. A peptide is considered to comprise at least one cryptic epitope if a T cell line can be established with a given peptide and T cells are capable of proliferation upon challenge with the peptide and the protein antigen from which the peptide is derived.

It is also possible to modify the structure of any of the above-described peptides for use in accordance with the present invention for such purposes as increasing solubility (particularly desirable if the composition is to be injected), enhancing therapeutic or preventive efficacy, or stability (e.g., shelf life ex vivo, and resistance to proteolytic degradation in vivo). A modified peptide can be produced in which the amino acid sequence has been altered as compared to the native protein sequence from which it is derived, or as compared to the peptide to be modified such as by amino acid substitution, deletion, or addition, to modify immunogenicity, or to which a component has been added for the same purpose. For example, WO 94/06828 describes substituted peptides in which essentially every amino acid residue may be substituted with a conservative amino acid, an amino acid not found in nature, or alanine, and yet the substituted peptide is still capable of down regulating an antigen specific immune response In addition, many of the documents cited above disclose various modifications to peptides with defined amino acid compositions which have been shown to induce T cell non-responsiveness.

In addition, it is not necessary that a peptide used in accordance with the method of this invention be derived from a known antgenic protein. Any peptide comprising a defined sequence of amino acid residues or capable of down-regulating an antigen specific immune response to an antigen or autoantigen may be used in accordance with the method of the present invention. For example, peptides may be synthesized comprising a defined amino acid sequence not based on a known protein antigen sequence, and yet are capable of down regulating an antigen specific immune response e.g. the peptide mimics a T cell epitope of the protein antigen and causes down regulation of the immune response to that protein antigen, or causes down regulation of the immune response for another reason, such as it is derived from a bystander antigen. Without being limited to any theory, it is believed that bystander antigens, which are also tissue specific (but are not the target of immune or autoimmune attack) possess the ability to elicit suppressor T cells at the site of immune attack which may in turn result in down regulating the immune responses in the locality of the immune attack (e.g. afflicted "self" tissue in the case of autoimmune disease or nasal mucosa, skin and lung in the case of allergy). Bystander antigens include but are not limited to portions of the antigen which are not themselves the target of immune attack, and which possess suppressive activity at the site of immune attack.

In addition, any compound that mimics a peptide capable of down regulating an antigen specific immune response to an antigen or autoantigen may be used in accordance with the invention. Such a compound may not be composed entirely of subunits joined by peptide bonds, but joined by other linkages (e.g. thiolester bonds), providing that the non-peptide compound mimics a peptide capable of down regulating an antigen specific immune response to the antigen of interest as indicated by effective therapeutic/prophylactic treatment of symptoms.

Additionally, peptide compositions administered in accordance with the invention preferably comprise a sufficient percentage of the T cell epitopes of the offending protein antigen (i.e. at least about 10% and more preferably about 20%, more preferably about 30%, more preferably about 40%, and even more preferably about 60% or greater, of the T cell reactivity to an offending antigen of interest) are included in the composition such that a therapeutic regimen of administration of the composition to an individual sensitive to a particular protein antigen in accordance with the invention, results in T cells of the individual being rendered nonresponsive to the protein antigen. To determine whether a peptide (candidate peptide) or a combination of candidate peptides are likely to contain a sufficient percentage of T cell epitopes of the protein antigen of interest to induce T cell nonresponsiveness in a substantial percentage of a population of individuals sensitive to the protein antigen, an algorithm can be used. In accordance with one such algorithm, a human T cell stimulation index (discussed above) for the peptide(s) in an in vitro T cell proliferation assay is calculated for each individual tested in a population of individuals sensitive to the protein antigen of interest. The remaining peptides in the in vitro T cell proliferation assay are overlapping peptides (overlapping by between about 5–15 amino acid residues) which cover the remainder of the protein not covered by the candidate peptide(s), which remaining peptides are at least about 12 amino acids long and which are preferably no longer than 30 and more preferably no longer than 25 amino acid residues in length. A human T cell stimulation index for each such remaining peptide in the set of peptides produced in the in vitro T-cell proliferation assay with T-cells obtained from each individual in the population of individuals tested is calculated and added together. For each individual, the human T cell stimulation index for the candidate peptide(s) is divided by the sum of the human T cell stimulation indices of the remaining peptides in the set of peptides tested to determine a percent. This percent is obtained for at least twenty (20) and preferably at least thirty (30) individuals sensitive to the protein antigen of interest and a mean percent is determined. A mean percent of about 10%, preferably about 20%, preferably about 30% and even more preferably about 50% or greater for the candidate peptide(s) together with a percent positive (defined as the percentage of positive T cell responses (S.I.s of greater than or equal to 2.0) in response to the candidate peptide or combination of candidate peptides) of at least about 60%, preferably about 75% and more preferably about 90% indicates that the candidate peptide(s) selected is likely to contain a sufficient percentage of T cell epitopes to induce T cell non responsiveness in a substantial percentage of a population of individuals sensitive to the protein antigen of interest.

For the treatment of allergy in accordance with the methods of the invention, it is preferred that a peptide used in conjunction therewith does not bind immunoglobulin E (IgE) or binds IgE to a substantially lesser extent (i.e. at least 100-fold less binding and more preferably, at least 1,000-fold less binding) than the protein allergen from which the peptide is derived binds IgE. The major complications of standard immunotherapy are IgE-mediated responses such as anaphylaxis. Immunoglobulin E is a mediator of anaphylactic reactions which result from the binding and cross-linking of antigen to IgE on mast cells or basophils and the release of mediators (e.g., histamine, serotonin, eosinophil chemotacic factors) in allergic ("atopic") patients. Thus, anaphylaxis in a substantial percentage of a population of individuals sensitive to the allergen being treated could be avoided by the use in immunotherapy of a peptide or peptides which do not bind IgE in a substantial percentage (e.g., at least about 75%) of a population of individuals sensitive to a given allergen, or if the peptide binds IgE, such binding does not result in the release of mediators from mast cells or basophils. The risk of anaphylaxis could be reduced by the use in immunotherapy of a peptide or peptides which have reduced IgE binding. Moreover, peptides which have minimal IgE stimulating activity are desirable for therapeutic effectiveness. Minimal IgE stimulating activity refers to IgE production that is less than the amount of IgE production and/or IL-4 production stimulated by the native protein allergen (e.g., Der p I). If a peptide binds IgE, it is preferable that such binding does not result in the release of mediators (e.g. histamines) from mast cells or basophils. To determine whether a peptide which binds IgE results in the release of mediators, a histamine release assay can be performed using standard reagents and protocols obtained for example, from Amac, Inc. (Westbrook, Me.). Briefly, a buffered solution of a peptide to be tested is combined with an equal volume of whole heparinized blood from an allergic subject. After mixing and incubation, the cells are pelleted and the supernatants are processed and analyzed using a radio immunoassay to determine the amount of histamine released.

Highly purified peptides free from all other polypeptides and contaminants having a defined sequence of amino acid residues comprising at least one T cell epitope, used in therapeutic compositions of this invention, may be produced synthetically by chemical synthesis using standard techniques. Various methods of chemically synthesizing peptides are known in the art such as solid phase synthesis which has been fully or semi automated on commercially available peptide synthesizers. Synthetically produced peptides may then be purified to homogeneity (i.e. at least 90%, more preferably at least 95% and even more preferably at least 97% purity), free from all other polypeptides and contaminants using any number of techniques known in the literature for protein purification.

In accordance with one procedure for producing highly purified homogenous peptide compositions, a peptide produced by synthetic chemical means (either anchored to a polymer support "solid phase synthesis" or by conventional homogenous chemical reactions "solution synthesis") may be purified by preparative reverse phase chromatography. In this method, the synthetically produced peptide in "crude" form is dissolved in an appropriate solvent (typically an aqueous buffer) and applied to a separation column (typically a reverse phase silica based media, in addition, polymer or carbon based media may be used). Peptide is eluted from the column by increasing the concentration of an organic component (typically acetonitrile or methanol) in an aqueous buffer (typically TFA, triethylamine phosphate, acetate or similar buffer). Fractions of the eluate will be collected and analyzed by appropriate analytical methods (typically reverse phase HPLC or CZE chromatography). Those fractions having the required homogeneity will be pooled. The counter ion present may be changed by additional reverse phase chromatography in the salt of choice or by ion exchange resins. The peptide may then be isolated as its acetate or other appropriate salt. The peptide is then filtered and the water removed (typically by lyophilization) to give a homogenous peptide composition containing at least 90%, more preferably at least 95% and even more preferably at least 97% of the required peptide component. Optionally, or in conjunction with reverse phase HPLC as described above, purification may be accomplished by affinity chromatography, ion exchange, size exclusion, counter current or normal phase separation systems, or any combination of these methods. Peptide may additionally be concentrated using ultra filtration, rotary evaporation, precipitation, dialysis or other similar techniques.

The highly purified homogenous peptide composition is then characterized by any of the following techniques or combinations thereof: a) mass spectroscopy to determine molecular weight to check peptide identity; b) amino acid analysis to check the identity of the peptide via amino acid composition; c) amino acid sequencing (using an automated protein sequencer or manually) to confirm the defined sequence of amino acid residues; d) HPLC (multiple systems if desired) used to check peptide identity and purity (i.e. identifies peptide impurities); e) water content to determine the water concentration of the peptide compositions; f) ion content to determine the presence of salts in the peptide composition; and g) residual organics to check for the presence of residual organic reagents, starting materials, and/or organic contaminants.

Synthetically produced peptides of the invention comprising up to approximately forty-five amino acid residues in length, and most preferably up to approximately thirty amino acid residues in length are particularly desirable as increases in length may result in difficulty in peptide synthesis. Peptides of longer length may be produced by recombinant DNA techniques as discussed below.

Peptides useful in the methods of the present invention may also be produced using recombinant DNA techniques in a host cell transformed with a nucleic acid sequence coding for such peptide. When produced by recombinant techniques, host cells transformed with nucleic acid encoding the desired peptide are cultured in a medium suitable for the cells and isolated peptides can be purified from cell culture medium, host cells, or both using techniques known in the art for purifying peptides and proteins including ion-exchange chromatography, ultra filtration, electrophoresis or immunopurification with antibodies specific for the desired peptide. Peptides produced recombinantly may be isolated and purified to homogeneity, free of cellular material, other polypeptides or culture medium for use in accordance with the methods described above for synthetically produced peptides.

In certain limited circumstances, peptides may also be produced by chemical or enzymatic cleavage of a highly purified full length or native protein of which the sites of chemical digest or enzymatic cleavage have been predetermined and the resulting digest is reproducible. Peptides having defined amino acid sequences can be highly purified and isolated free of any other poly peptides or contaminants present in the enzymatic or chemical digest by any of the procedures described above for highly purified, and isolated synthetically or recombinantly produced peptides.

Highly purified and isolated peptides produced as discussed above may be formulated into therapeutic compositions of the invention suitable for human therapy. If a therapeutic composition of the invention is to be administered by injection (i.e. subcutaneous injection), then it is preferable that the highly purified peptide be soluble in an aqueous solution at a pharmaceutically acceptable pH (i.e. pH range of about 4–9) such that the composition is fluid and easy syringability exists. The composition also preferably includes a pharmaceutically acceptable carrier. As used herein "pharmaceutically acceptable carrier" includes any and all excipients, solvents, dispersion media, coatings, antibacterial and antifungal agents, toxicity agents, buffering agents, absorption delaying or enhancing agents, surfactants, and miclle forming agents, lipids, liposomes, and liquid complex forming agents, stabilizing agents, and the like. The use of such media and agents for pharmaceutically active substance is known in the art. Except insofar as any conventional media or agent is incompatible with the active compound, use thereof in the therapeutic compositions is contemplated. Supplementary active compounds can also be incorporated into the compositions.

Therapeutic compositions of the invention suitable for injectable use are preferably sterile aqueous solutions prepared by incorporating active compound (i.e., one or more highly purified and isolated peptide as described above) in the required amount in an appropriate vehicle with one or a combination of ingredients enumerated above and below, as required, followed by filtered sterilization. Preferred pharmaceutically acceptable carriers include at least one excipient such as sterile water, sodium phosphate, mannitol, sorbitol, or sodium cloride or any combination thereof. Other pharmaceutically acceptable carriers which may be suitable include solvents or dispersion medium containing, for example, water, ethanol, polyol (for example glycerol, propylene glycol, and liquid polyethylene glycol, and the like), suitable mixtures thereof, and vegetable oils. The proper fluidity can be maintained for example by the use of coating such as lecithin, by the maintenance of the required particle size in the case of dispersions and by the use of surfactants. Prevention of the action of microorganisms can be achieved by various antibacterial and antifungal agents, for example, parabens, chlorobutanol, phenol, ascorbic acid, thirmerosol and the like. Prolonged absorption of the injectable compositions can be brought about by including in the composition, an agent which delays absorption, for example, aluminum monostearate and gelatin.

A therapeutic composition of the invention should be sterile, stable under conditions of manufacture, storage, distribution and use and should be preserved against the contaminating action of microorganisms such as bacteria and fungi. A preferred means for manufacturing a therapeutic compositions of the invention in order to maintain the integrity of the composition (i.e. prevent contamination, prolong storage, etc.) is to prepare the formulation of peptide and pharmaceutically acceptable carrier(s) such that the composition may be in the form of a lyophilized powder which is reconstituted in a pharmaceutically acceptable carrier, such as sterile water, just prior to use. In the case of sterile powders for the preparation of sterile injectable solutions, the preferred methods of preparation are vacuum drying, freeze-drying or spin drying which yields a powder of the active ingredient plus any additional desired ingredient from a previously sterile-filtered solution thereof. Specific formulations of therapeutic compositions of the invention are described below and in the Examples.

In many cases, a therapeutic composition of the invention comprises more than one isolated peptide. A therapeutic composition comprising a multipeptide formulation suitable for pharmaceutical administration to humans may be desirable for administration of several active peptides. The multipeptide formulation includes at least two or more isolated peptides having a defined amino acid sequence and is capable of down regulating an antigen specific immune response. Special considerations when preparing a multipeptide formulation include maintaining the solubility, and stability of all peptides in the formulation in an aqueous solution at a physiologically acceptable pH. This requires choosing one or more pharmaceutically acceptable solvents and excipients which are compatible with all the peptides in the multipeptide formulation. For example, suitable excipients include sterile water, sodium phosphate, mannitol or both sodium phosphate and mannitol. An additional consideration in a multipeptide formulation is the prevention of dimerization of the peptides if necessary. Agents may be included in the multipeptide formulation which prevent dimerization such as EDTA or any other material or procedures known in the art to prevent dimerization. The following is an example of the multipeptide formulation used in a Phase II human clinical trial as a therapeutic for the treatment of allergies to cat. Two active peptides, peptide X (SEQ ID NO 1) and peptide Y (SEQ ID NO 2), each having a defined composition of amino acid residues, and derived from the protein allergen Fel d I, were synthesized via chemical synthesis and purified to homogeneity as described above for use in a multipeptide formulation for treating humans allergic to cats in accordance with the present invention. For this embodiment, Peptide X (SEQ ID NO 1) and Peptide Y (SEQ ID NO 2) were in the form of a lyophilized powder which was reconstituted in sterile water, prior to use. Peptide X (SEQ ID NO 1) and Peptide Y (SEQ ID NO 2) were combined during manufacturing using known techniques to produce a vial containing a sterile, pyrogen free, lyophilized powder having the following composition:

| | |
|---|---|
| Active: | 0.75 mg peptide X (SEQ ID NO 1) and 0.75 mg peptide Y (SEQ ID NO 4) |
| Inactives: | 0.05M Sodium Phosphate, pH 6.2 5% w/v Mannitol, U.S.P. |
| Diluent: | Sterile Water for Injection, U.S.P. (initial reconstitution) 0.9% Sodium Chloride for Injection (dilution beyond initial reconstitution) |

Preparation of this multipeptide formulation requires reconstitution of the vials with sterile water for injection. In another embodiment, the multipeptide formulation may further include three (see Example 2), four, five or more additional peptides suitable for human therapy.

Administration of the therapeutic compositions as described above to an individual, in a non-immunogenic form, can be carried out using known procedures at dosages and for periods of time effective to cause down regulation of the antigen specific immune response (i.e., reduce the disease symptoms of antigen specific immune response caused by the offending antigen) of the individual. Down regulation of an antigen specific immune response to an antigen associated with a disease condition in humans may be determined clinically whenever possible depending on the disease condition being treated, or may be determined subjectively (i.e. the patient feels as if some or all of the symptoms related to the disease condition being treated have been alleviated).

Effective amounts of the therapeutic compositions of the invention will vary according to factors such as the degree of sensitivity of the individual to the antigen, the age, sex, and weight of the individual, and the ability of peptide to cause down regulation of the antigen specific immune response in the individual. A therapeutic composition of the invention may be administered in non-immunogenic form, in a convenient manner such as by injection (subcutaneous, intravenous, etc.), oral administration, subligual, inhalation, transdermal application, rectal administration, or any other route of administration known in the art for administering therapeutic agents It may be desirable to administer simultaneously or sequentially a therapeutically effective amount of one or more of the therapeutic compositions of the invention to an individual. Each of such compositions for administration simultaneously or sequentially, may comprise only one peptide or may comprise a multipeptide formulation as described above.

For subcutaneous injection of one or more therapeutic compositions of the invention, preferably about 1 $\mu$g–3 mg and more preferably from about 20 $\mu$g–1.5 mg, and even more preferably about 50 $\mu$g–750 $\mu$g of each active component (peptide) per dosage unit may be administered. It is especially advantageous to formulate parenteral compositions in unit dosage form for ease of administration and uniformity of dosage. Unit dosage form as used herein refers to physically discrete units suited as unitary dosages for human subjects to be treated; each unit containing a predetermined quantity of active compound calculated to produce the desired therapeutic effect in association with the desired pharmaceutical carrier. The specification for the novel unit dosage forms of the invention are dictated by and directly dependent on (a) the unique characteristics of the active compound and the particular therapeutic effect to be achieved, and (b) the limitations inherent in the art of compounding such an active compound for the treatment of human subjects.

Dosage regimen may be adjusted to provide the optimum therapeutic response. For example, several divided doses may be administered over the course of days, weeks, months or years, or the dose may be proportionally increased or reduced with each subsequent injection as indicated by the exigencies of the therapeutic situation. In one preferred therapeutic regimen, subcutaneous injections of therapeutic compositions are given once a week for 3–6 weeks. The dosage may remain constant for each injection or may increase or decrease with each subsequent injection. A booster injection may be administered at intervals of about three months to about one year after initial treatment and may involve only a single injection or may involve another series of injections similar to that of the initial treatment.

To administer a composition of the invention by other than parenteral administration, (i.e. oral administration) it may be necessary to coat the composition with, or co-administer the composition with, a material to prevent its inactivation or enhance its absorption and bioavailability. For example, a peptide formulation may be co-administered with enzyme inhibitors or in liposomes. Enzyme inhibitors include pancreatic trypsin inhibitor, diisopropylfluorophosphate (DEP) and trasylol. Liposomes include water-in-oil-in-water CGF emulsions as well as conventional liposomes (Strejan et al., (1984) *J. Neuroimmunol.*, 7:27). When a peptide is suitably protected, the peptide may be orally administered, for example, with an inert diluent or an assimilable edible carrier. The peptide and other ingredients may also be enclosed in a hard or soft shell gelatin capsule, compressed into tablets, or incorporated directly into the individual's diet. For oral therapeutic administration, the active compound may be incorporated with excipients and used in the form of ingestible tablets, buccal tablets, troches, capsules, elixirs, solutions, gels, suspensions, syrups, wafers, and the like. Such compositions and preparations should contain at least 1% by weight of active compound. The percentage of the composition and preparations may, of course, be varied and may conveniently be between about 5 to 80% of the weight of the unit. The amount of active compound in such therapeutically useful compositions is such that a suitable dosage will be obtained. In addition, the active compound may be incorporated into sustained-release or controlled release (steady state or pulsatile release) preparations and formulations.

This invention is illustrated by the following non-limiting examples.

EXAMPLE 1

Administration of Peptides to Human Subjects for Treatment of Allergy to Cat

A. Composition of Phase I Formulation

For Phase I clinical trials the drug product was comprised of two freeze-dried peptide formulations, peptide X (SEQ ID NO 1) and peptide Y (SEQ ID NO 2). Peptide X (SEQ ID NO 1) and peptide Y (SEQ ID NO 2) were manufactured separately, and packaged into two distinct pyrogen free vials.

| PEPTIDE X (SEQ ID NO 1) | |
|---|---|
| Active: | 1.5 mg/vial |
| Inactives: | 0.1M Sodium Phosphate, pH 5.7 |
| | 5% w/v Mannitol, U.S.P. |
| Diluent: | Sterile Water for Injection, U.S.P. |
| PEPTIDE Y (SEQ ID NO 2) | |
| Active: | 1.5 mg/vial |
| Inactives: | 0.1M Sodium Phosphate, pH 5.7 |
| | 5% w/v Mannitol, U.S.P. |
| Diluent: | Sterile Water for Injection, U.S.P. |

In this study, the drug product was supplied in two separate vials as sterile, pyrogen free, lyophilized powders containing sodium phosphate and mannitol as excipients, and the active component peptide X (SEQ ID NO 1) or peptide Y (SEQ ID NO 2).

Preparation of the drug product in these studies required reconstitution of the vials with sterile water for injection. Dilution of reconstituted vials was required to deliver lower doses in the dose titration concentrations of 7.5 or 75 µg/mL, and also. accomplished using sterile 0.9% sodium chloride for injection. If desired, the vials could have been prepared with only 7.5 or 75 µg per peptide without need for dilutions.

The lyophilized drug product was stored at or below −20° C. and the drug product was administered immediately after reconstitution. These storage conditions and use conditions are not limiting.

B. Composition of Phase II Formulation

For Phase II clinical trials a single formulation containing 750 µg/ml final concentration of each peptide was developed. Peptide X (SEQ ID NO 1) and peptide Y (SEQ ID NO 2) were combined during the fill finish process to produce a vial containing a sterile, pyrogen free, lyophilized powder.

| | |
|---|---|
| Active: | 0.75 mg peptide X (SEQ ID NO 1) and 0.75 mg peptide Y (SEQ ID NO 4) |
| Inactives: | 0.05M Sodium Phosphate, pH 6.2 |
| | 5% w/v Mannitol, U.S.P. |
| Diluent: | Sterile Water for Injection, U.S.P. (initial reconstitution) |
| | 0.9% Sodium Chloride for Injection (dilution beyond initial reconstitution) |

The freeze-dried drug product was reconstituted to 750 µg/ml concentration with sterile water for injection. Dilution of reconstituted vials for lower doses, e.g., to achieve concentrations of 7.5 or 75 µg/mL, was accomplished using sterile 0.9% sodium chloride for injection. Subjects were administered the drug product according to the administration instructions contained in the clinical protocol.

The drug product was administered immediately after reconstitution.

The lyophilized drug product was stored at or below −20° C., however, this is not limiting.

D. Human Phase I and II Clinical Studies

The following Phase I and Phase II studies of peptides X and Y (SEQ ID NOS: 1 and 2) have been conducted in human cat-allergic subjects.

Protocol P92–01: Phase I Clinical Study of Safety and Activity of Peptides X and Y This Phase I, open-label, dose-escalating safety study was conducted to determine the safety of the administration of the peptide X (SEQ ID NO 1) and peptide Y (SEQ ID NO 2). The antigenicity of the components was also evaluated, as was the activity of the peptides in altering skin test sensitivity.

Two centers, Johns Hopkins Asthma and Allergy Center, Baltimore, Md. and New England Medical Center, Boston, Mass., enrolled a total of nineteen (19) cat-allergic individuals in this study. Peptide X (SEQ ID NO 1) and peptide Y (SEQ ID NO 2) were administered separately but concomitantly by subcutaneous injections in escalating doses ranging from 7.5 µg to 1500 µg over a five-week period.

Safety was assessed by evaluations of clinical laboratory parameters, physical examination, antibody studies and adverse experiences. Activity was assessed by analysis of skin testing. Prick and intradermal skin testing with both affinity purified native Fel d I and the peptides were performed one week prior to, and two and six weeks following the treatment period. Sixteen patients were treated with peptides X and Y during the study. The peptides were well tolerated at doses of up to 1500 µg. There were no serious adverse experiences and the safety of the peptides to justify further clinical development was confirmed. Adverse events recorded with the trial were typical of those seen in open label allergy studies. Patients were all cat allergic individuals in this trial and tolerated dose orders of magnitude higher than can be achieved with conventional immunotherapy.

One patient discontinued the study due to an asthma attack which occurred following skin testing with cat extract I and peptides on Week 1, and a second asthma attack which occurred following the 7.5 µg dose of each peptide on Week 2. It is unclear whether there is a direct relationship between treatment with the peptides and the onset of asthma in this patient. It is noteworthy that the study was conducted during one of the most severe pollen seasons of recent years and this patient, like many of those enrolled, had seasonal allergies.

Antibody studies revealed that all evaluable patients had IgG and IgE antibodies to Fel d I. In all but two patients, the concentrations did not change over the course of the study. Two patients demonstrated IgE antibodies to peptide X (SEQ ID NO 1) and/or peptide Y (SEQ ID NO 2) at Weeks 8 and 12 which were not present at Week 1. One of these patients had a substantial skin test reaction to peptide X (SEQ ID NO 1) at Week 8 which was not present at Week 12. Five patients had endogenous IgG antibody to peptide X (SEQ ID NO 1) and three patients had IgG antibody to peptide Y (SEQ ID NO 2) prior to exposure to the peptides. Four patients with no pre-existing, anti-peptide IgG antibodies to peptide X (SEQ ID NO 1) and/or peptide Y (SEQ ID NO 2) developed increased concentrations of such antibodies during or after treatment. Two patients developed a positive immediate skin test reaction to a treatment peptide during the study but without clinical correlation. Another patient had a delayed local reaction to skin testing with peptide Y (SEQ ID NO 2) at Week 8 which was related to the intradermal dose of peptide Y (SEQ ID NO 2).

Skin test results to cat allergen showed a statistically-significant decrease in reactivity to cat extract containing Fel d I at two or three dilutions by prick test after 8 or 12 weeks, respectively. No statistically significant differences in reactivity were detected by the intradermal method. There was a statistically-significant decrease in the late phase reactivity to Fel d I ($\Sigma_E$) at six and twenty-four hours at the Johns Hopkins site when Week 8 was compared to baseline (Week 1). The decrease was not significant when Week 12 was compared to baseline.

Although this study was designed to evaluate safety, the skin testing data suggested that the peptides may be causing desensitization to Fel d I.

Protocol P92–02: Phase II Clinical Study of the Safety and Activity of Peptides X and Y Using a Cat Room Challenge Model This phase II safety and efficacy study was a double blind placebo-controlled study of peptides X and Y given subcutaneously in four weekly doses of 7.5 µg, 75 µg, or 750 µg per peptide. Patient's sensitivity to natural exposure was assessed by measurement of symptom scores and pulmonary function during a 60-minute period in a small room containing stuffed furniture and two cats. This cat room challenge occurred pretreatment and one and six weeks posttreatment. In the cat room, patients rated nose, eye and lung symptoms on a five point scale every five minutes. Pulmonary function was tested every 15 minutes. Additional parameters assessed during the study were skin test sensitivity to cat extract and peptides X and Y, specific IgE and IgG to Fel d I and component peptides X and Y, and T cell responsiveness to cat antigen and selected peptides.

Ninety-five patients were enrolled at two centers, Johns Hopkins Asthma and Allergy Center, Baltimore, Md. and New England Medical Center, Boston, Mass. Ninety-one patients completed the trial. Four patients discontinued, two because of transient allergic symptoms associated with the therapy and two because of scheduling conflicts.

The therapy was generally well tolerated. Analysis of the primary efficacy data for the study revealed a significant dose response relationship which was considered statistically significant (FIG. 1) for control of allergic symptoms (nasal, lung, and total allergy) induced by cat room exposure at one and six weeks posttreatment. Statistically significant pairwise comparisons versus placebo for nasal and total allergy symptoms at 75 ; µg and 750 µg was detected at six weeks (See FIG. 1). The 7.5 µg dose could not be distinguished from placebo. Patients were prick test negative to study medication pretreatment, but 13 patients had positive prick and/or intradermal skin test to treatment peptides. Two patients developed significant titres of IgE to treatment peptide and were skin test positive to study medication post-treatment. Only five patients with positive skin tests to peptide had measurable IgE to peptide. A proportion of patients (placebo: 57.7%; 7.5 µg: 60.9%; 75 µg: 63.6%; 750 µg: 83.3%) reported cat-allergic symptoms such as rhinorrhea, nasal congestion, pruritus, chest tightness, and/or wheezing during this study. The study medication appeared to induce some mild transient symptoms suggestive of natural cat exposure. The incidence was dose-related (placebo: 11.5–19.2%; 7.5 µg: 21.7–26.1%; 75 µg: 31.8–45.5%; and 750 µg: 50.0–62.5%). Such symptoms were generally mild, self limited and required no treatment or were controlled with beta agonist and/or antihistamine. One patient was treated with adrenaline, and six patients had asthmatic symptoms with drop in peak flow. All were managed easily. The treatment did not alter antibody responses to call allergies in the time period studied, did not effect skin teat reactivity relative to placebo, but was associated with improvement of total allergy score in 80% of study patients. Additional studies to better characterize the treatment effect are underway.

EXAMPLE 2

Administration of Peptides to Humans for Treatment of Allergy to Ragweed

A. Phase I Formulation

For Phase I clinical trials, the drug product was a multi-peptide formulation comprising three freeze-dried peptides of Amb a I, the sequence of amino acid residues of each comprising at least one T cell epitope of the ragweed protein allergen Amb a I.1 (see, WO93/21321, incorporated herein by reference). Each peptide was purified to homogeneity (at least 97% pure) in accordance with the methods described above. The multipeptide formulation was prepared in accordance with procedures described herein. The multipeptide formulation used in this Phase I clinical Study was in the form of a freeze-dried powder cake of each the of peptides in a single vial. The formulation was reconstituted just prior to use with sterile water for injection and normal saline (0.9%) was used for any dilutions beyond the initial reconstitution.

B. Human Phase I Clinical Studies

Preliminary data indicated that all doses were tolerated and the multipeptide formulation appears to be safe. Further analysis and Phase II Clinical Studies are pending in the United States and Canada.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. A method of treating allergy in humans comprising administering to a human at least one therapeutic composition in an amount sufficient to down regulate a protein allergen specific immune response in the human, wherein the therapeutic composition comprises at least one isolated peptide having a defined sequence of amino acid residues, said peptide comprising at least about 20% of the T cell epitopes of the protein allergen, said peptide being reproducible and not being conjugated to any other molecule, said peptide having a mean T cell stimulation index of at least about 3.5determined in an in vitro T cell proliferation assay with T cell obtained from a population of humans sensitive to said allergen, and said peptide having a positivity index of at least 150 as determined in an in vitro T cell proliferation assay with T cell obtained from a population of humans sensitive to said allergen, wherein the composition is first administered at three to six dosages of said composition once a week for three to six weeks.

2. The method of claim 1 further comprising a second administration of said composition at intervals of between about three months and one year after said first administration.

3. The method of claim 1, wherein the peptide comprises 50 amino acid residues or less.

4. The method as in any one of claims 1 or 3, further comprising the step of increasing the dosage with each subsequent additional dosage of said composition.

5. The method as in any one of claims 1 or 3, wherein treatment results in a statistically significant improvement in symptoms caused by the human's immune response to the protein allergen.

6. The method as in any one of claims 1 or 3, wherein the peptide is modified by at least one amino acid substitution, addition or deletion, said peptide comprising a T cell epitope recognized by a T cell receptor specific for the protein allergen.

7. The method as in any one of claims 1 or 3, wherein the peptide is purified to at least 90% purity.

8. The method of claim 7, wherein the peptide is purified to at least 95% purity.

9. The method of claim 8, wherein the peptide is purified to at least 97% purity.

10. The method as in any one of claims 1 or 3, wherein the peptide is at least about 12 amino acid residues in length.

11. The method as in any one of claims 1 or 3, wherein the at least one peptide comprises at least two peptides.

12. The method as in any one of claims 1 or 3, wherein the protein allergen is selected from the group consisting of: a protein allergen of the genus Dermatophagoides; a protein allergen of the genus Felis; a protein allergen of the genus Ambrosia; a protein allergen of the genus Lolium; a protein allergen of the genus Cryptomeria; a protein allergen of the genus Alternaria; a protein allergen of the genus Alder; a protein allergen of the genus Betula; a protein allergen of the genus Quercus; a protein allergen of the genus Olea; a protein allergen of the genus Artemisia; a protein allergen of the genus Plantago; a protein allergen of the genus Parietaria; a protein allergen of the genus Canine; a protein allergen of the genus Blattella; a protein allergen of the genus Apis; a protein allergen of the genus Cupressus; a protein allergen of the genus Juniperus; a protein allergen of the genus Thuya; a protein allergen of the genus Chamaecyparis; a protein allergen of the genus Periplaneta; a protein allergen of the genus Agropyron; a protein allergen of the genus Secale; a protein allergen of the genus Triticum; a protein allergen of the genus Dactylis; a protein allergen of the genus Festuca; a protein allergen of the genus Poa; a protein allergen of the genus Avena; a protein allergen of the genus Holcus; a protein allergen of the genus Anthoxanthum; a protein allergen of the genus Arrhenatherum; a protein allergen of the genus Agrostis; a protein allergen of the genus Phleum; a protein allergen of the genus Phalaris; a protein allergen of the genus Paspalum; and a protein allergen of the genus Sorghum.

13. The method of claim 12, wherein the protein allergen is selected from the group consisting of; Der p I; Der p II; Der p III; Der p VII; Der f I; Der f II; Der f III; Der f VII; Fel d I; Amb a I.1; Amb a I.2; Amb a I.3; Amb a I.4; Amb a II; Lol p I, Lol p II; Lol p III; Lol p IV; Lol p IX (Lol p V or Lol p Ib); Cry j I; Cry j II; Can fI; Can f II; Jun s I; Jun v I; Dac g I; Poa p I; Phl p I; and Sor h I.

14. The method as in any one of claims 1 or 3, wherein the composition further comprises a pharmaceutically acceptable carrier.

15. The method of claim 14, wherein the pharmaceutically acceptable carrier comprises at least one excipient selected from the group consisting of sterile water, sodium phosphate, mannitol, sorbitol, sodium chloride, and any combination thereof.

16. The method as in any one of claims 1 or 3, wherein the composition soluble in an aqueous solution at a physiologically acceptable pH.

17. The method as in any one of claims 1 or 3, wherein said administering comprises a route of administration selected from the group consisting of oral, intravenous, sublingual, transdermal, inhalation, subcutaneous and rectal.

18. The method of claim 17, wherein said administering comprises subcutaneous administration of said composition.

19. The method as in any one of claims 1 or 3, wherein said composition is administered without adjuvant.

20. A method of treating allergy in humans comprising administering to a human at least one therapeutic composition in an amount sufficient to down regulate a protein allergen specific immune response in the human, wherein the therapeutic composition comprises at least one isolated peptide having a defined sequence of amino acid residues, said peptide comprising at least about 20% of the T cell epitopes of the protein allergen, said peptide being reproducible and not being conjugated to any other molecule, said peptide having a mean T cell stimulation index of at least about 3.5 determined in an in vitro T cell proliferation assay with T cells obtained from a population of humans sensitive to said allergen, and said peptide having a positivity index of at least 150 as determined in an in vitro T cell proliferation assay with T cells obtained from a population of humans sensitive to said allergen, comprising the step of decreasing the dosage with each subsequent additional dosage of said composition.

* * * * *